(12) United States Patent
Weffers-Albu

(10) Patent No.: US 11,213,233 B2
(45) Date of Patent: Jan. 4, 2022

(54) ASSESSING DELIRIUM IN A SUBJECT

(71) Applicant: KONINKLIJKE PHILIPS N.V., Eindhoven (NL)

(72) Inventor: Mirela Alina Weffers-Albu, Boukoul (NL)

(73) Assignee: Koninklljke Philips N.V., Eindhoven (NL)

( * ) Notice: Subject to any disclaimer, the term of this patent is extended or adjusted under 35 U.S.C. 154(b) by 599 days.

(21) Appl. No.: 16/020,001

(22) Filed: Jun. 27, 2018

(65) Prior Publication Data

US 2019/0000368 A1 Jan. 3, 2019

(30) Foreign Application Priority Data

Jun. 28, 2017 (EP) .................... 17178492

(51) Int. Cl.
*A61B 5/16* (2006.01)
*A61B 5/01* (2006.01)
*A61B 5/00* (2006.01)
*A61B 5/369* (2021.01)
*A61B 5/145* (2006.01)
(Continued)

(52) U.S. Cl.
CPC ............... *A61B 5/165* (2013.01); *A61B 5/01* (2013.01); *A61B 5/14535* (2013.01); *A61B 5/369* (2021.01); *A61B 5/4815* (2013.01); *A61B 5/4836* (2013.01); *A61B 5/024* (2013.01); *A61B 5/0816* (2013.01); *A61B 5/4845* (2013.01); *A61B 2505/01* (2013.01); *A61B 2560/0242* (2013.01)

(58) Field of Classification Search
CPC ........... A61B 5/165; A61B 5/369; A61B 5/01; A61B 5/14535; A61B 5/4815; A61B 5/4836; A61B 5/024; A61B 5/0816; A61B 5/4845; A61B 2505/01; A61B 2560/0242
USPC ...................................................... 600/301
See application file for complete search history.

(56) References Cited

U.S. PATENT DOCUMENTS

2005/0159987 A1 7/2005 Rosenfeld et al.
2009/0270692 A1* 10/2009 Hyde ..................... A61B 5/024
600/301
(Continued)

FOREIGN PATENT DOCUMENTS

EP 2323056 A1 5/2011
WO 2015200434 A1 12/2015

OTHER PUBLICATIONS

Brummel, N. et al., "Implementing Delirium Screening in the Intensive Care Unit: Secrets to Success", Crit Care Med. Sep. 2013; 41(9): 2196-2208.
(Continued)

*Primary Examiner* — Aaron F Roane

(57) ABSTRACT

There is provided a system (100) for assessing delirium in a subject. The system includes a neural activity assessment module (102) for assessing neural activity data associated with the subject. The system also includes a delirium cause assessment module (104) for assessing data relating to at least one factor of a plurality of factors which contribute to the cause of delirium. The system also includes an intervention determination module (106) for determining, based on the assessment performed by the delirium cause assessment module, at least one intervention for reducing the contribution made by the at least one factor. A computer-implemented method and an apparatus are also disclosed.

15 Claims, 3 Drawing Sheets

(51) Int. Cl.
*A61B 5/024* (2006.01)
*A61B 5/08* (2006.01)

(56) References Cited

U.S. PATENT DOCUMENTS

2010/0016751 A1  1/2010  Hunter et al.
2015/0363567 A1  12/2015  Pettus

OTHER PUBLICATIONS

Cerejeira, J. et al., "A Clinical Update on Delirium: From Early Recognition to Effective Management", Hindawi Publishing Corporation, Nursing Research and Practice, vol. 2011, Article ID 875196, 12 pages, Apr. 2011.
Van Der Kooi, A. et al., "Electroencephalography-based monitoring of delirium in the ICU: what are the opportunities?", 32nd International Symposium on Intensive Care and Emergency Medicine, Mar. 20, 2012, https://ccforum.biomedcentral.com/articles/10.1186/cc10945.
"Delirium", Mayo Clinic, Apr. 18, 2018, https://www.mayoclinic.org/diseases-conditions/delirium/symptoms-causes/syc-20371386.
"Delirium: diagnosis, prevention and management", National Clinical Guideline Centre, Clinical Guideline 103, Jul. 2010.
CHEST Journal, Official Publication of the American College of CHEST Physicians, 2018, https://journal.chestnet.org/.
Van Der Kooi, A. et al., "Delirium Detection Using EEG: what and how to measure", Jan. 2015, vol. 147, Issue 1, pp. 94-101.
Prolira, "Detecting Delirium", accessed Jun. 19, 2018, http://prolira.com/.
"Objective Delirium Detection With an Innovative EEG-Based Spot Monitor—Delirium Monitor", Narcis, 2015, https://www.narcis.nl/research/RecordID/OND1358739.
Alagiakrishnan, K., "Delirium Treatments Management", Medscape, Mar. 21, 2018, https://emedicine.medscape.com/article/288890-treatment.
Collins, N. et al., "Detection of delirium in the acute hospital", Age and Ageing, vol. 39, Issue 1, Jan. 1, 2010, pp. 131-135, https://academic.oup.com/ageing/article/39/1/131/41152.
Mistraletti, G. et al., "Sleep and delirium in the intensive care unit", 74(6):329-33, Jul. 2008.
Sedesse, P., "Causes of Low Hematocrit Blood Test Results", http://www.explain-health.com/Causes-low-hematocrit-blood-test-anemia.html, 2011.
Mahmood, N. et al., "Methodology for EEG Based System Development to Detect Objective Pain in Human Body", International Journal of Scientific & Engineering Research, vol. 3, Issue 11, Nov. 2012.
Vatankhah, M. et al., "Pain Level Measurement Using Discrete Wavelet Transform", International Journal of Engineering and Technology, vol. 8, No. 5, Oct. 2016.
Middleton, C., "Understanding the physiological effects of unrelieved pain", Nursing Times, Sep. 16, 2003, https://www.nursingtimes.net/clinical-archive/pain-management/understanding-the-physiological-effects-of-unrelieved-pain/205262.article.
Hannu Koponen et al, EEG spectral analysis in delirium, Journal of Neurology, Neurosurgery, and Psychiatry 1989;52:980-985.

* cited by examiner

ASSESSING DELIRIUM IN A SUBJECT

CROSS-REFERENCE TO PRIOR APPLICATIONS

This application claims the benefit of European Patent Application No. 17178492.9, filed on 28 Jun. 2017. This application is hereby incorporated by reference herein.

TECHNICAL FIELD OF THE INVENTION

The invention relates to assessing delirium in a subject and, more particularly, to assessing delirium in a subject and determining an intervention.

BACKGROUND TO THE INVENTION

Delirium is a disturbance in a person's mental abilities that leads to confused thinking and reduced awareness of the person's environment. Onset of delirium can occur within hours or a few days, and is often caused by a medical illness, a change in a person's metabolic balance, medication, infection, surgery, or withdrawal from alcohol or drugs.

People suffering from delirium often suffer multiple symptoms, such as hallucinations, restlessness, agitation, calling out, becoming quiet or withdrawn, lethargy and disturbed sleep.

Hospital patients, particularly those who have been admitted to an intensive care unit (ICU), are prone to suffering from delirium, and many ICU patients exhibit signs of suffering from delirium before they arrive at the ICU. Some people are at higher risk of developing symptoms of delirium. For example, older people, people who have been diagnosed with dementia, depression or alcoholism, people with a history of sight loss or hearing loss, people with impaired mobility, and people who have a history of changing mental status are at greater risk of suffering from delirium. In some cases, a trigger event, or a series of events may lead to a person becoming delirious.

Undetected or unmanaged delirium can lead to increased morbidity, increased length of stay in a hospital, the development of dementia, an increased risk of falling and, as a consequence of these, significantly increased patient costs.

In currently-used approaches, trained medical professionals often observe a patient over a period of time, and interview the patient to establish their mental state, then decide whether or not the patient is showing signs of suffering from delirium. The medical professional may observe the patient's symptoms over time to assist with their diagnosis. However, many of the symptoms of delirium are also symptoms of other health issues and, therefore, a patient exhibiting symptoms associated with delirium might not actually be suffering from delirium but, rather, might be suffering from separate illnesses.

Therefore, it would be desirable to have a means for accurately assessing delirium in a person and, if the person has delirium, then reducing the symptoms and the risk that the delirium will develop further.

SUMMARY OF THE INVENTION

Existing methods of assessing delirium and symptoms of delirium in a person rely on a subjective assessment based on human observations and interviews where a person provides their view of how they are feeling. In order to accurately determine whether a person is suffering from delirium, which factor or factors are causing the delirium, and how the delirium might be treated, it would be useful to have a system which performs an objective assessment and provides an accurate assessment of the factors contributing to the delirium.

According to a first aspect, the present invention provides a system for assessing delirium in a subject. The system comprises a neural activity assessment module for assessing neural activity data associated with the subject; a delirium cause assessment module for assessing data relating to at least one factor of a plurality of factors which contribute to the cause of delirium; and an intervention determination module for determining, based on the assessment performed by the delirium cause assessment module, at least one intervention for reducing the contribution made by the at least one factor.

By using neural activity data to assess whether or not the subject is suffering from delirium, an accurate assessment can be made, and a proactive decision can be made as to whether to provide an intervention. Thus, the assessment is objective. Furthermore, the assessment can be made relatively quickly, and in real time. In other existing systems, a prolonged subjective assessment of the subject may be required before it can be determined whether or not the subject is suffering from delirium. If is it determined that the subject is not suffering from delirium, then preventative measures can be taken to reduce the risk of developing delirium in the future, as assessment of data relating to the contributory factors will provide an indication of the factors most likely to lead to the onset of delirium.

Since one or more contributory factors are assessed, it is possible to determine the likely cause, or contributing factors of the cause of delirium. In this way, any interventions can be targeted to the relevant contributing factor. Furthermore, interventions may be selected which do not cause other medical problems. Thus, the interventions can be personalised to the subject, and are intended to deal with specific factors that cause delirium.

In some embodiments, the neural activity data may comprise data acquired using electroencephalogram (EEG) measurements of the subject's brain. EEG measurements are accurate and, therefore, an accurate assessment of whether or not the subject is suffering from delirium can be made.

The plurality of factors may comprise: a likelihood that the subject will develop an infection; a measure of pain suffered by the subject; a measure of a quality of sleep experienced by the subject; a likelihood that medication being taken by the subject will cause delirium; and a measure associated with the subject's environment. In some embodiments, the delirium cause assessment module may assess data relating to all of these factors. By combining the assessment of data all of the factors of the plurality of factors, a better understanding of the causes of the delirium can be achieved and, as a result, a more effective determination of the interventions needed to reduce the contributions, or to alleviate the symptoms of delirium for the subject, can be made.

The likelihood that the subject will develop an infection may, in some embodiments, be determined based a measure of the subject's core body temperature and a measure of the subject's haematocrit levels. By using technical data such as this, the assessment can be accurate, and the determination of the infection risk can be more objective.

In some embodiments, the measure of pain may be determined based at least on the neural activity data. The measure of pain may be determined further based on at least one of acquired respiratory data of the subject and acquired heart rate data of the subject.

Using technical data obtained using medical measurement techniques such as these means that the measure of pain suffered by the subject can be accurately and objectively determined, rather than the subjective view that might be obtained by asking the subject to provide their opinion of the level of pain they are suffering.

The likelihood of the subject's medication causing delirium may, in some embodiments, be determined based on an assessment of a plurality of other subjects, each of the plurality of other subjects having a medical profile similar to a medical profile of the subject.

In some embodiments, the measure of the subject's environment may be acquired using audio capturing equipment and image capturing equipment to capture data relating to at least one of: illumination levels in the subject's environment, noise levels in the subject's environment and numbers of people visiting the subject. Using these non-invasive measurement techniques means that the environment can be monitored continuously and objectively, and suitable interventions can be applied easily, if desired.

A weight may be applied to at least one of the plurality of factors, the weight of a given factor being based on the contribution of the given factor to the cause of delirium for the subject. By weighting the factors according to importance, or according to their relative contribution to the cause of delirium, the overall risk of the subject developing delirium can be more relevant.

The delirium cause assessment module may, in some embodiments, be configured to assess data relating to a plurality of factors which contribute to the cause of delirium. The delirium cause assessment module may be configured to determine a delirium risk for the subject based on a combination of the data relating to the plurality if factors. As noted above, by combining data of multiple factors, a more accurate assessment of the delirium risk can be achieved and, consequently, a more effective set of interventions may be determined, targeting those factors that contribute the most towards the delirium.

In some embodiments, the intervention determination module may be configured to determine the at least one intervention further based on health record data associated with the subject. The intervention determination module may be configured to determine at least one intervention for reducing the contribution made by one of the plurality of factors, wherein the at least one intervention does not increase the contribution made by any other of the plurality of factors. Selecting interventions in this way means that the treatment to be provided to the subject may be targeted and aimed at alleviating symptoms of particular contributory factors. Interventions can be selected with do not cause other health problems, contribute to the cause of delirium in some other way.

According to a second aspect, the present invention provides a computer-implemented method for assessing delirium in a subject. The method comprises acquiring neural activity data for the subject; determining whether the acquired neural activity is indicative that the subject is suffering from delirium; acquiring data relating to at least one factor of a plurality of factors which contribute to the cause of delirium; and determining, based on the acquired data relating to the at least one factor, at least one intervention for reducing the contribution made by the at least one factor.

In some embodiments, the computer-implemented method may further comprise indicating the determined at least one intervention to a medical professional.

According to a third aspect, the present invention provides an apparatus for assessing delirium in a subject. The apparatus comprises a memory comprising instruction data representing a set of instructions; and a processor configured to communicate with the memory and to execute the set of instructions, wherein the set of instructions, when executed by the processor, cause the processor to: receive neural activity data for the subject; determine whether the received neural activity is indicative that the subject is suffering from delirium; receive data relating to at least one factor of a plurality of factors which contribute to the cause of delirium; and determine, based on the received data relating to the at least one factor, at least one intervention for reducing the contribution made by the at least one factor.

Other advantageous features will become apparent from the following description.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF EMBODIMENTS

The present disclosure provides an improved system for assessing delirium in a subject. The term "subject", in the context of this disclosure may be considered to be any person. The subject does not need to be located in a medical environment, such as in a hospital; however, the system may be implemented within a medical institution, and subjects located in such a medical institution may be referred to as patients.

A subject may be assessed initially using brain monitoring techniques, such as electroencephalography (EEG). Electroencephalography is a monitoring method which records electrical activity of the brain, using electrodes placed on the subject's scalp. Some EEG signals can be representative of delirium characteristics and, therefore, analysis of the EEG readings can be used to determine whether or not the subject is suffering from delirium. More specifically, a relative power of a particularly frequency band in the EEG output, known as the theta frequency band, may be significantly different in a subject suffering from delirium than in a subject who is not suffering from delirium. EEG readings of a subject may also be used to determine if the subject is suffering from early stages of delirium.

A subject may be monitored using EEG when there is a suspicion that they are suffering from, or likely to suffer from, delirium. For example, a subject who is admitted to hospital, or a subject (i.e. a patient) who is being treated in an intensive care unit (ICU) of a hospital, may be monitored using EEG, as such subjects may be at higher risk of suffering from delirium. If, from EEG readings of a subject's brain activity, it is determined that the subject is already suffering from delirium, then action may be taken to manage the delirium, and prevent symptoms from becoming worse. If, however, it is determined from the EEG readings that the subject is not suffering from delirium, then the subject may be monitored continuously, or repeatedly (e.g. periodically) to detect any onset of delirium, and action may be taken to reduce the likelihood that the subject will suffer an episode of delirium.

Embodiments of the invention disclosed herein relate to systems, apparatus and methods for assessing delirium, which may make use of data obtained from EEG readings of a subject.

Figure 1:
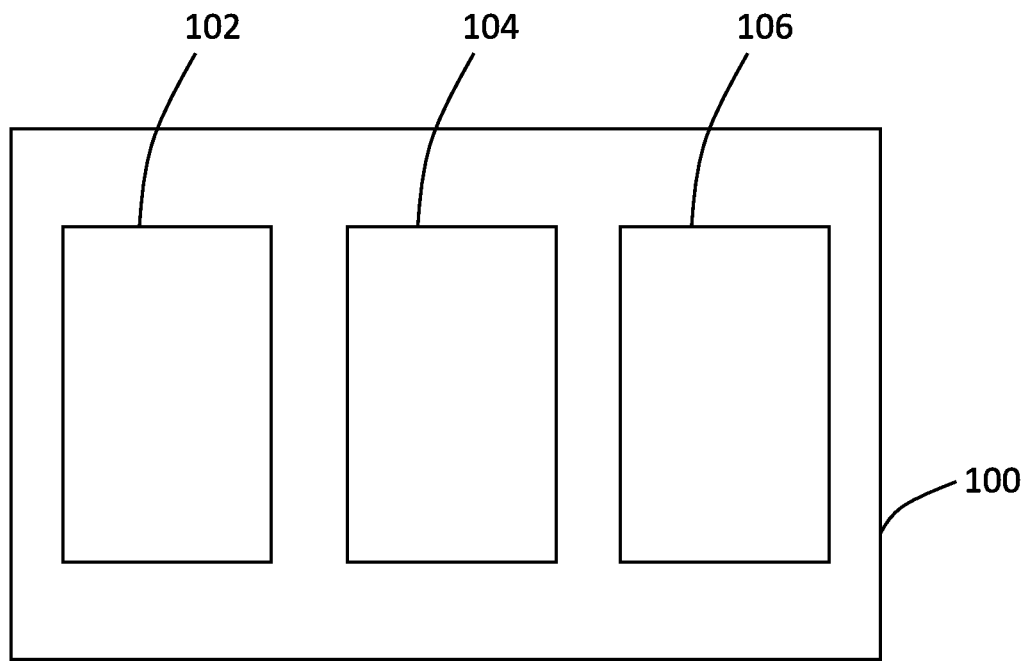
FIG. 1 is a schematic illustration of an example of a system for assessing delirium in a subject, according to embodiments of the invention.

Referring to the drawings, FIG. 1 shows, schematically, an example of a system 100 for assessing delirium in a subject. The system 100 comprises a neural activity assessment module 102 for assessing neural activity data associated with the subject. The neural activity data may be acquired in real time, for example from EEG sensors positioned on the subject's head, such that real time neural activity data may be acquired and analysed. Alternatively, the neural activity data may be obtained from a storage medium (e.g. a database) containing previously-recorded (preferably recently-recorded) neural activity data of the subject. In this way, the system 100 may still be able to assess the subject, without the need for constant EEG monitoring of the subject's brain.

The neural activity assessment module 102 may analyse neural activity data and output a value, or score, indicative of the likely severity of delirium of the subject based on their brain activity. The output value/score may correspond to the difference in the measured power of the theta frequency band from the an average value of the power of the theta frequency band of non-delirious subjects, which may be obtained from measurements taken from a group of subjects with a similar clinical profile to the subject being monitored. In other words, the larger the difference in the subject's measured theta power from the average theta power of non-delirious subjects, the larger the value/score output by the neural activity assessment module 102. Similarly, the closer the measured theta power is to an average theta power of a group of delirious subjects with a similar clinical profile to the subject being monitored, the smaller lower the output value/score. The output from the neural activity assessment module 102 may, in some embodiments, be referred to as a "NeuralActivityScore", and may be a numerical value.

A relatively high, or increasing, neural activity score may be indicative of developing or pronounced delirium characteristics in the subject, while a relatively low, or decreasing, neural activity score may be indicative of improving neural activity, and reduced delirium characteristics in the subject.

The system 100 further comprises a delirium cause assessment module 104 for assessing data relating to at least one factor of a plurality of factors which contribute to the cause of delirium. The delirium cause assessment module 104 may take into account data relating to one, some or all of the plurality of factors which contribute to the cause of delirium for the subject. Details of the contributory factors, and how data relating to the factors might be obtained is discussed below. In general, however, data may be obtained in real time from one or more sensors connected to the system 100, such that a real time assessment of the data may be performed by the delirium cause assessment module 104. Alternatively, previously-recorded or previous-acquired data may be obtained, for example from a storage medium and assessed by the delirium cause assessment module 104.

The system 100 further comprises an intervention determination module 106 for determining, based on the assessment performed by the delirium cause assessment module 104, at least one intervention for reducing the contribution made by the at least one factor. An intervention is intended to include, for example, an action or a change of behaviour, which can help to alleviate one or more symptoms of delirium, help to limit the development of delirium in the subject and/or help the reduce the likelihood that the subject will suffer from delirium. Examples of types of intervention are discussed below with reference to the factors that may be affected as a result of the interventions.

The system 100 may be implemented as a collection of computer software modules (102, 104, 106) configured to operate on a computer system, such as a desktop computer, a laptop computer, a tablet computer or a smartphone. In some embodiments, the system 100 may be implemented over multiple computing devices or servers, and may be implemented partly or fully in a cloud computing environment.

As noted above, the neural activity data may, in some embodiments, comprise data acquired using electroencephalography, EEG, measurements of the subject's brain. In such embodiments, the system 100 may further comprise, or be connected to, an EEG device for monitoring the subject's brain.

Numerous factors may contribute to delirium and, particularly, to symptoms related to delirium which a subject may experience. In some embodiments, the plurality of factors which contribute to the cause of delirium may comprise a likelihood that the subject will develop an infection; a measure of pain suffered by the subject; a measure of a quality of sleep experienced by the subject; a likelihood that medication being taken by the subject will cause delirium; and a measure associated with the subject's environment. Other factors may also be relevant and data from other factors may additionally be taken into account by the delirium cause assessment module 104. While, in some embodiments, delirium cause assessment module 104 may assess data relating to just one of the plurality of factors, in other embodiments, the delirium cause assessment module may assess data relating to multiple factors of the plurality of factors. Thus, in some embodiments, a subset of these factors may be assessed. A more reliable assessment of delirium in the subject may be achieved if multiple factors are taken in to account. In one embodiment, data relating to all five of the factors listed above may be assessed. The combination of data from multiple factors, particular from the five factors mentioned above, may provide a more accurate assessment, and may enable a more appropriate determination of interventions to be made. Thus, the provision of a suitable intervention, or set of interventions, to alleviate the effects of delirium in the subject may be improved by assessing multiple factors, or all five of the factors mentioned above.

In some embodiments, data relating the at least one factor may be assessed over a period of time, so that any patterns or trends in the data may become apparent. For example, a factor may be assessed over a period of an hour, or twenty four hours. By assessing a factor over a period of time, it may be possible to determine if the contribution by that factor to the delirium is increasing, decreasing or remaining relatively constant.

Figure 2:
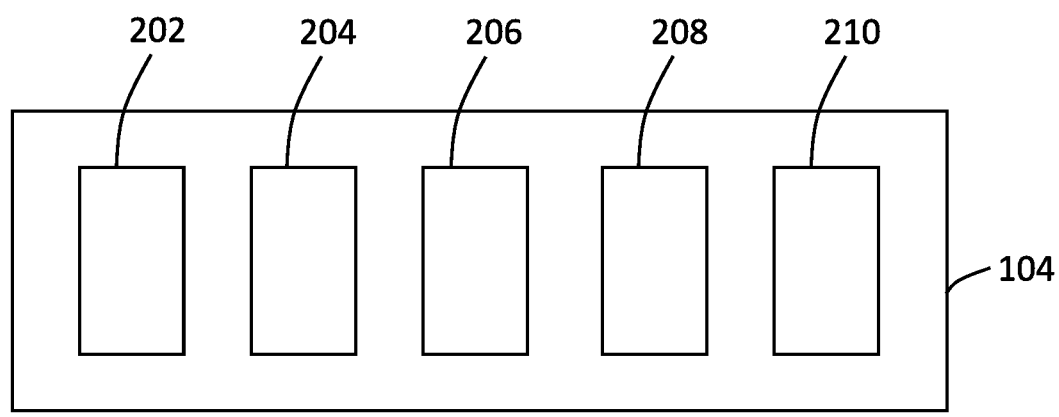
FIG. 2 is a schematic illustration of an example of a first module of the system of FIG. 1.

FIG. 2 is a schematic illustration of an example of the delirium cause assessment module 104 of FIG. 1. The delirium cause assessment module 104 may include a sub-module for each of the plurality of factors that may be taken into account in the assessment made by the delirium cause assessment module. Each sub-module may assess data relating to a respective factor of the plurality of factors. The delirium cause assessment module 104 may comprise an infection sub-module 202, a pain sub-module 204, a quality of sleep sub-module 206, a medication sub-module 208 and an environment sub-module 210.

A first factor of the plurality of factors is a likelihood that the subject will develop an infection, or an infection risk of the subject, and this may be assessed by the infection sub-module 202. This factor relates to the likelihood the subject will develop an infection, for example, over an upcoming period of time, or during a stay in a medical institution, such as a hospital.

The likelihood that the subject will develop an infection may, in some embodiments, be determined based a measure of the subject's core temperature and a measure of the subject's haematocrit levels. Thus, in some embodiments, the system 100 may comprise, or be connected to a device for measuring a core temperature (e.g. an internal body temperature) of the subject, and a device for measuring the subject's haematocrit levels. In other embodiments, the temperature measurements and the haematocrit measurements may be delivered to, or input into the system 100 for assessment by the infection sub-module 202, or the delirium cause assessment module 104 from a remote source.

The haematocrit (Ht) is a volume percentage of red blood cells in a subject's blood. Low or decreasing levels of haematocrit combined with a high and/or increasing core temperature may be indicative that an infection is developing within the subject. The haematocrit may, in some embodiments, be measured using an imaging device, such as a camera configured to measure a subject's vital signs, and a light source configured to illuminate the subject's skin with light of a particular wavelength to which the camera is sensitive.

The data obtained from the core temperature measurement (referred to as "core_temperature") and the haematocrit measurement (referred to as "haematocrit_level") may be used to calculate an infection risk score (referred to as "InfectionRiskScore"). For example, the infection risk score may be calculated according to the following formula:

$$\text{InfectionRiskScore} = \text{core\_temperature} \otimes \text{haematocrit\_level} \quad [1]$$

where $\otimes$ represents a generic symbol, meaning that the terms may be combined in some way.

In some embodiments, a weight may be applied to one or more of the core temperature measurement and the haematocrit measurement based, for example, on an assessment of how the values are changing over time. For example, if, over a period of time, the core temperature measurements follow a trend to increase rapidly, then this might be a significant contributory factor to the cause of delirium. Thus, the core temperature measurement may be weighted heavily compared to the haematocrit measurement.

Thus, in some particular embodiments, the infection risk score may be calculated according to the following formula:

$$\text{InfectionRiskScore} = \text{core\_temperature} \times \text{weight\_temp} + \text{haematocrit\_level} \times \text{weight\_haematocrit} \quad [2]$$

where weight_temp is the weight applied to the core temperature measurement and weight_haematocrit is the weight applied to the haematocrit measurement.

A second factor of the plurality of factors is a measure of pain suffered by the subject, and this may be assessed by the pain sub-module 204. This factor relates to the detection of pain incidents, measuring both the intensity of the pain and duration that the pain is experienced by the subject. The intensity of pain may be classified in three levels: (i) no pain, (ii) pain, and (iii) unbearable pain. In some embodiments, the pain measurement data may be assessed in real time. That is to say, pain measurements may be acquired and analysed straight away.

Different regions within a subject's brain are responsible for different functions, and various regions of the brain are responsible for detecting pain. For example, the parietal lobe, the anterior parietal lobe, the superior parietal lobe and the inferior parietal lobe may all be responsible for detecting pain. Thus, the measure of pain may, in some embodiments, be determined based at least on the neural activity data. Thus, the pain measurements may be made using an EEG device, such as the EEG device used to measure the neural activity data assessed by the neural activity assessment module 102. In this way, data from the brain activity monitoring can be used for multiple uses.

Using EEG readings to determine a measure of pain suffered by the subject, it is possible to differentiate between the "no pain" and pain intensity levels (i.e. "pain"/"unbearable pain"). A frequency band known as the alpha EEG frequency band can be used to indicate the presence of pain in a subject. Distinguishing between the "no pain" and "any level of pain" classifications may be achieved by investigating signal wavelet coherency of EEG signals, and by investigating changes occurring during different levels of pain intensity. When a subject transitions from a baseline pain level (i.e. no pain) to some level of pain, the brain phase changes significantly and, therefore, the coherence between EEG signals during the "no-pain" and some pain levels (i.e. "pain"/"unbearable pain") is clearly evident.

The EEG readings can also be used to distinguish between the "pain" and "unbearable pain" intensity levels. High levels of pain may have an impact on the respiratory and cardiac function of a subject, caused, for example, by a subject limiting the movement of their thoracic and abdominal muscles in a bid to reduce pain. Furthermore, the cardiovascular system may respond to the stress of pain by increasing sympathetic nervous system activity which, in turn, may increase the subject's heart rate, blood pressure and peripheral vascular resistance. In terms of the respiratory signal, this may cause shallow breathing, compensated by faster breathing to increase the amount of oxygen intake. These traits may be reflected in a respiratory signal that has a significant lower amplitude and shorter respiratory cycle during an "unbearable pain" episode. Thus, in some embodiments, the measure of pain may be determined further based on at least one of acquired respiratory data of the subject and acquired heart rate data of the subject.

Thus, if the EEG readings indicate that the subject is experiencing some level of pain, but none of the above traits characteristic to "unbearable pain" are detected in respiratory and heart signals, then the pain sub-module 204 or the neural activity assessment module 102 may classify the detected event as "pain". However, if some level of pain is detected in the EEG readings, and traits characteristic to "unbearable pain" are detected in respiratory and heart signals, then the pain sub-module 204 or the neural activity assessment module 102 may classify the detected event as "unbearable pain".

In some embodiments, additional classifications of pain may be used.

The pain sub-module 204 may output a pain level score (referred to as "PainLevelScore") which may, in some embodiments, be a numerical value associated with the level of pain.

A third factor of the plurality of factors is a measure of a quality of sleep experienced by the subject, and this may be assessed by the quality of sleep sub-module 206. This factor relates to the quality of sleep experienced by a subject, either in real time, or over a period of time, such as overnight. The quality of sleep sub-module 206 assesses data relating to the subject's quality of sleep by quantifying the sleep quality based on detected sleep onset latency, the sleep duration, a number of wake events and the sleep duration during the night time.

The quality of sleep sub-module 206 may output a quality of sleep score (referred to as "QoSScore") which may, in some embodiments, be a numerical value.

A fourth factor of the plurality of factors is a likelihood that medication being taken by the subject will cause delirium, and this may be assessed by the medication sub-module 208. This factor relates to a risk caused by medications administered to the subject. In some embodiments, the likelihood of the subject's medication causing delirium may be determined based on an assessment of a plurality of other subjects, each of the plurality of other subjects having a medical profile similar to a medical profile of the subject. That is to say, data associated with a group of medically similar subjects is analysed and used to determine the risk that a particular medication or medications administered to the subject will contribute to cause delirium. For example, the data may be used to quantify the risk of the subject developing delirium if they are administered particular medications, such as tranquillizers, benzodiazepines, and anticholinergic medications. The likelihood of the subject developing delirium may increase if a larger dosage of a medication is administered.

The medication sub-module 208 may output a medication risk score (referred to as "MedicationRiskScore") which may, in some embodiments, be a numerical value.

A fifth factor of the plurality of factors is a measure associated with the subject's environment, and this may be assessed by the environment sub-module 210. This factor relates to the contribution to the cause of delirium from parameters of the environment relative to the subject. In some embodiments, the environmental parameters may include the level of illumination, the level of noise and level of interaction of the subject with other people. Insufficient illumination, high noise levels, particularly noise which disturbs the subject's sleep, and isolation can all contribute to the cause of delirium in a subject. All of these elements may have an impact on the subject's ability to maintain a sense of orientation, which may be desirable in reducing the development of delirium.

The environment sub-module 210 may output an environment risk score (referred to as "EnvironmentRiskScore") which may, in some embodiments, be a numerical value. In some embodiments, the three contributory environmental factors may be monitored continuously, for example using suitable components, in order to calculate a real time contribution made by environmental factors. For example, in some embodiments, the measure of the subject's environment may be acquired using audio capturing equipment and image capturing equipment to capture data relating to at least one of: illumination levels in the subject's environment, noise levels in the subject's environment and numbers of people visiting the subject.

The delirium cause assessment module 104 may use data from one or more of the factors discussed above in order to determine an overall risk score for the subject developing delirium.

The delirium risk score (referred to as "DeliriumRiskScore") may be determined based on a combination of the outputs of one or more of the sub-modules 202-210 discussed above. Thus, the delirium cause assessment module 104 may be configured to assess data relating to a plurality of factors which contribute to the cause of delirium. The delirium cause assessment module 104 may be configured to determine a delirium risk for the subject based on a combination of the data relating to the plurality of factors. In some embodiments, the delirium cause assessment module 104 may use data from all five factors discussed above. In other words, the delirium risk score may be calculated based on the scores determined for all of the factors discussed above. In some embodiments, the delirium risk score may be calculated as follows:

$$\text{DeliriumRiskScore} = \text{InfectionRiskScore} \otimes \text{PainLevelScore} \otimes \text{QoSScore} \otimes \text{MedicationRiskScore} \otimes \text{EnvironmentRiskScore}. \quad [3]$$

By using data relating to multiple contributory factors, particularly from all five factors discussed above, a better understanding of the relevant factors that are causing the subject to suffer from, or develop, delirium can be achieved. A better understanding of the cause of delirium means that a more targeted and effective intervention strategy can be determined. In this way, the subject is likely to overcome the delirium more quickly or, if the subject has not yet developed delirium, then the risk factors most likely to cause delirium can be managed, thereby reducing the risk of the subject becoming delirious.

In some scenarios, for example when the EEG readings of a subject indicate that the subject is not suffering from delirium, the neural activity score may be taken into account when calculating the delirium risk score. In such scenarios, the delirium risk score may be calculated as follows:

$$\text{DeliriumRiskScore} = \text{NeuralActivityScore} \otimes \text{InfectionRiskScore} \otimes \text{PainLevelScore} \otimes \text{QoSScore} \otimes \text{MedicationRiskScore} \otimes \text{EnvironmentRiskScore}. \quad [4]$$

For any of the factors, the output values (e.g. scores) may be weighted according to the relative importance of the contributory factor. In some embodiments, a weight may be applied to at least one of the plurality of factors, the weight of a given factor being based on the contribution of the given factor to the cause of delirium for the subject.

In an embodiment in which the scores are weighted, the delirium risk score may be calculated as follows:

$$\text{DeliriumRiskScore} = \text{NeuralActivityScore} \times \text{weight\_1} + \text{InfectionRiskScore} \times \text{weight\_2} + \text{PainLevelScore} \times \text{weight\_3} + \text{QoSScore} \times \text{weight\_4} + \text{MedicationRiskScore} \times \text{weight\_5} + \text{EnvironmentRiskScore} \times \text{weight\_6} \quad [5]$$

where weight_1 to weight_6 represent weighting factors to be applied to their respective scores.

As noted above, the intervention determination module 106 is configured to determine, based on the assessment performed by the delirium cause assessment module 104, at least one intervention for reducing the contribution made by the at least one factor. The intervention determination module 106 may generate a personalised set of interventions for a particular subject, intended to help the subject to avoid delirium onset if they are not already suffering from delirium, or to reduce the effects of delirium if they are already suffering from delirium. In some embodiments, the intervention determination module 106 may be configured to determine at least one intervention only if the delirium risk score calculated by the delirium cause assessment module 104 exceeds a threshold value. In other words, if there is a high enough likelihood that the subject will develop delirium, then the intervention determination module 106 will determine one or more appropriate interventions.

When it is determined that the intervention determination module 106 is to determine one or more interventions, an intervention may be selected for any contributory factor which exhibits indications that its contribution to the cause of delirium is increasing. In other words, if it is determined that data for a particular factor appears to be following a trend to increase (i.e. its contribution is increasing), then an intervention may be selected. In some embodiments, interventions may be selected from a set of interventions suitable for the various factors.

For example, if the InfectionRiskScore value appears to be increasing over time, indicating subject deterioration in resulting from a potential infection, then the system 100 may contact a medical professional to inform them of the increasing infection risk score, and to request approval to administer antibiotics and medications to reduce the onset of the infection.

The interventions may, in some embodiments, be determined based on data other than the assessments made by the delirium cause assessment module 104. For example, in some embodiments, the intervention determination module 106 may be configured to determine the at least one intervention further based on health record data associated with the subject. Health record data may be obtained, for example, from a medical database, or from an electronic health record (EHR) associated with the subject.

Any intervention selected by the intervention determination module 106, to be administered to the subject may, in some embodiments, be selected such that it does not have any adverse effect on the subject, or affect the other factors in an adverse manner. Thus, the intervention determination module 106 may be configured to determine at least one intervention for reducing the contribution made by one of the plurality of factors, wherein the at least one intervention does not increase the contribution made by any other of the plurality of factors. For example, if an intervention is selected to reduce the onset of an infection, identified from a high InfectionRiskScore value, then it is desirable that the selected intervention does not result in some other factor increasing. For example, it is desirable that a medication administered to reduce the infection onset does not cause the quality of sleep of the subject to reduce by preventing them from falling asleep.

Figure 3:
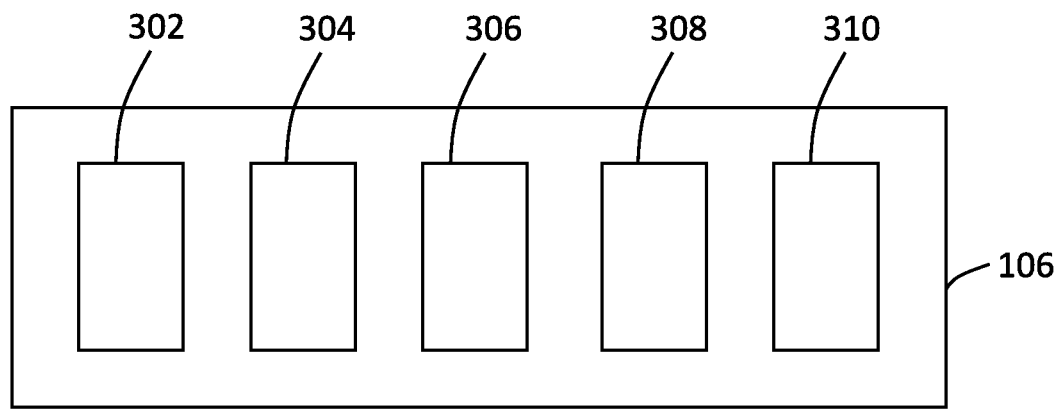
FIG. 3 is a schematic illustration of an example of a second module of the system of FIG. 1.

FIG. 3 is a schematic illustration of an example of the intervention determination module 106 of FIG. 1. The intervention determination module 106 may include an intervention, or set of interventions, for each of the plurality of factors discussed above. For example, as shown in FIG. 3, the intervention determination module 106 includes interventions for mitigating infection risk 302, interventions for mitigating pain 304, interventions for mitigating deteriorating quality of sleep 306, interventions for mitigating medication risk 308 and interventions for mitigating environmental risk 310. Each of the interventions selected from the intervention determination module 106 may be selected from the set of interventions 302-310. In some embodiments, one intervention may be selected while, in other embodiments, multiple interventions may be selected. For example, the intervention determination module 106 may select an intervention for each contributory factor relevant to the subject.

An example of an intervention for mitigating infection risk 302 is the administration of medication. An example of an intervention for mitigating pain 304 is the administration of pain relief medication. Examples of interventions for mitigating deteriorating quality of sleep 306 is the administration of sleeping tablets, or reducing the light or noise in a subject's room during the night. An example of an intervention for mitigating medication risk 308 is to review the administered medication and ensure that any medication does not affect any other factor that might contribute to the cause of delirium. Examples of interventions for mitigating environmental risk 310 is changing the lighting conditions in the subject's room, reducing the noise in the subject's room, and ensuring that the subject is visited regularly throughout the day.

In some embodiments, the system 100 may be configured to operate in different modes, depending on whether or not a subject is already suffering from delirium. For example, if, from the neural activity data, it is determined that the subject is not currently suffering from delirium, then the system 100 may operate in a "delirium risk assessment and prevention mode". In this mode, the risk of the subject developing delirium from any of the factors discussed above may be assessed, and the neural activity data may be assessed continuously or repeatedly to identify signs of an onset of delirium. The interventions determined in this mode are intended to reduce the risk that the subject will develop delirium. If, from the neural activity data, it is determined that the subject is currently suffering from delirium, then the system 100 may operate in a "delirium management mode". In this mode, the system 100 may determine a set of interventions, and continue to assess the data relating to the factors discussed above to determine whether or not the interventions are effective in managing the delirium. In some embodiments, if it is determined that an intervention is not helping to manage the delirium, then an additional and/or alternative intervention may be selected.

Embodiments of the present invention also relate to a method of assessing delirium in a subject. The method may be performed by a computing device, or a network of computing devices, servers or processing devices. The method may, in some embodiments, be carried out in a cloud-computing environment.

Figure 4:
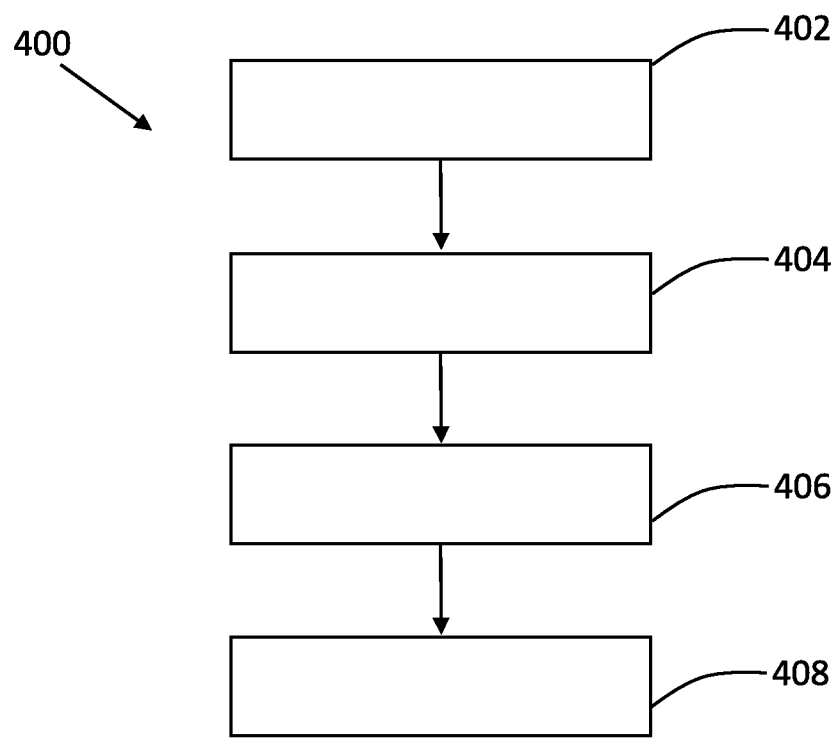
FIG. 4 is a flowchart of an example of a method of for assessing delirium in a subject, according to embodiments of the invention.

FIG. 4 is a flow chart of an example of a computer-implemented method 400 for assessing delirium in a subject. The method 400 comprises, at step 402, acquiring neural activity data for the subject. As noted above, the neural activity data may be acquired from a storage medium, such as a database stored in a memory, or from brain monitoring equipment, such as an EEG device. The method 400 further comprises, at step 404, determining whether the acquired neural activity is indicative that the subject is suffering from delirium. Using neural activity data of the subject, it is possible to determine accurately whether the subject is already suffering from delirium, of exhibiting signs that they are developing delirium. At step 406, the method comprises acquiring data relating to at least one factor of a plurality of factors which contribute to the cause of delirium. Some of the data may be acquired from the EEG device or other brain monitoring equipment used to acquire the neural activity data. Alternatively, if relevant neural activity data has already been acquired and stored in a storage medium, then the data acquired at step 406 may be obtained from the storage medium. The method comprises, at step 408, determining, based on the acquired data relating to the at least one factor, at least one intervention for reducing the contribution made by the at least one factor. Thus, one or more interventions may be selected or devised which will help to reduce the contribution to the cause of delirium by a particular contributory factor, or multiple contributory factors. In some embodiments, the determination of an intervention may comprise selecting an intervention from a plurality of interventions. The plurality of interventions may, for example, be stored in a database or look-up table, and each of the plurality of intervention may be associated with one or more contributory factors.

Figure 5:
FIG. 5 is a flowchart of a further example of a method of for assessing delirium in a subject, according to embodiments of the invention.

FIG. 5 shows a flow chart of a further example of a computer-implemented method 500 for assessing delirium in a subject. The method 500 may include one or more of the steps of the method 400 discussed above. The method 500 further comprises, at step 502, indicating the determined at least one intervention to a medical professional. Details of the intervention may, for example, be delivered to a mobile device of a medical professional, so that the medical professional is made aware that the subject is exhibiting signs of developing delirium, and then provided with details of a particular intervention which might be administered to the subject to reduce the contributions, of effects, of the contributory factor. In some embodiments, the determined at least one intervention may be displayed on a display, such as a screen of a computing device, and/or stored in a medical report (e.g. an EHR) of a subject to be reviewed by a medical professional.

Figure 6:
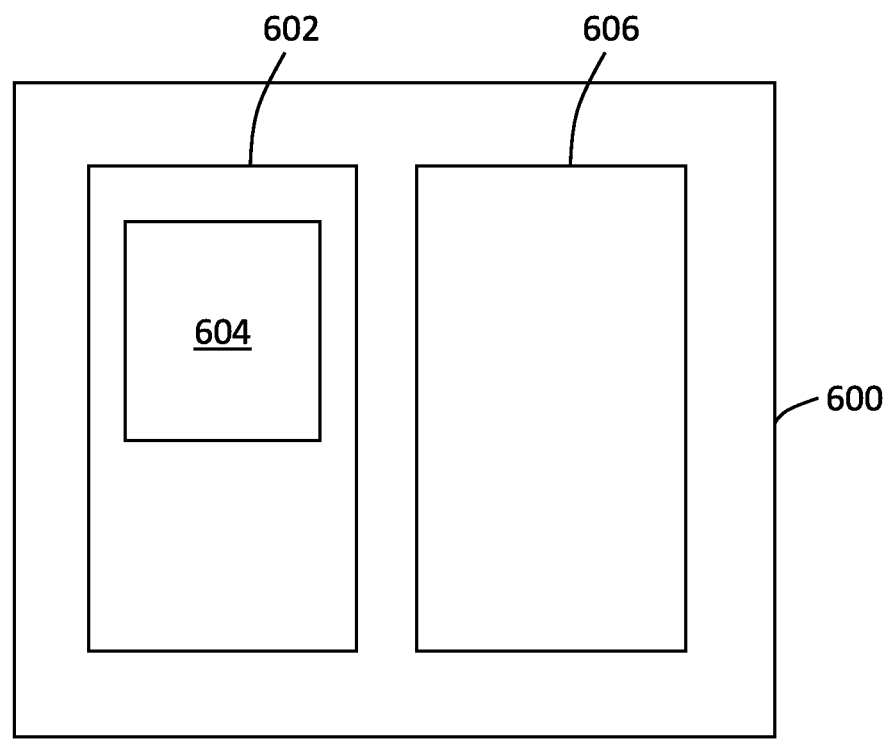
FIG. 6 is a schematic illustration of an example of an apparatus for assessing delirium in a subject.

As noted above, the system and/or the methods described above may be implemented on a computing device or as part of a computing network. FIG. 6 shows, schematically, an example of an apparatus 600 for assessing delirium in a subject. The apparatus comprises a memory 602 comprising instruction data 604 representing a set of instructions. The apparatus 600 also comprises a processor 606 configured to communicate with the memory 602 and to execute the set of instructions 604, wherein the set of instructions, when executed by the processor, cause the processor to receive neural activity data for the subject; determine whether the received neural activity is indicative that the subject is suffering from delirium; receive data relating to at least one factor of a plurality of factors which contribute to the cause of delirium; and determine, based on the received data relating to the at least one factor, at least one intervention for reducing the contribution made by the at least one factor. More generally, the apparatus 600 may be configured to perform the methods 400, 500 described above. Thus, the apparatus 600 may comprise a computing device.

The processor 606 can comprise one or more processors, processing units, multi-core processors or modules that are configured or programmed to control the apparatus 600 in the manner described herein. In particular implementations, the processor 606 can comprise a plurality of software and/or hardware modules that are each configured to perform, or are for performing, individual or multiple steps of the method described herein.

The term "module", as used herein is intended to include a hardware component, such as a processor or a component of a processor configured to perform a particular function, or a software component, such as a set of instruction data that has a particular function when executed by a processor.

It will be appreciated that the embodiments of the invention also apply to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to embodiments of the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at runtime. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A system for assessing delirium in a subject, the system comprising:
   a neural activity assessment module for assessing neural activity data associated with the subject;
   a delirium cause assessment module for assessing data relating to at least one factor of a plurality of factors which contribute to a cause of delirium, wherein the plurality of factors comprises a likelihood that the subject will develop an infection, wherein the likelihood that the subject will develop the infection is determined based on a measure of haematocrit levels of a subject; and
   an intervention determination module for determining, based on the assessment performed by the delirium cause assessment module, at least one intervention for reducing the contribution made by the at least one factor.

2. A system according to claim 1, wherein the neural activity data comprises data acquired using electroencephalogram, EEG, measurements of the subject's brain.

3. A system according to claim 1, wherein the plurality of factors comprises:
a measure of pain suffered by the subject;
a measure of a quality of sleep experienced by the subject;
a likelihood that medication being taken by the subject will cause delirium; and
a measure associated with the subject's environment.

4. A system according to claim 3, wherein the likelihood that the subject will develop the infection is determined further based on a measure of the subject's core body temperature.

5. A system according to claim 3, wherein the measure of pain is determined based at least on the neural activity data.

6. A system according to claim 5, wherein the measure of pain is determined further based on at least one of acquired respiratory data of the subject and acquired heart rate data of the subject.

7. A system according to claim 3, wherein the likelihood of the subject's medication causing delirium is determined based on an assessment of a plurality of other subjects, each of the plurality of other subjects having a medical profile similar to a medical profile of the subject.

8. A system according to claim 3, wherein the measure of the subject's environment is acquired using audio capturing equipment and image capturing equipment to capture data relating to at least one of: illumination levels in the subject's environment, noise levels in the subject's environment and numbers of people visiting the subject.

9. A system according to claim 1, wherein a weight is applied to at least one of the plurality of factors, the weight of a given factor of the at least one of the plurality of factors being based on the contribution of the given factor to the cause of delirium for the subject.

10. A system according to claim 1, wherein the delirium cause assessment module is configured to assess data relating to the plurality of factors which contribute to the cause of delirium; and
wherein the delirium cause assessment module is configured to determine a delirium risk for the subject based on a combination of the data relating to the plurality if factors.

11. A system according to claim 1, wherein the intervention determination module is configured to determine the at least one intervention further based on health record data associated with the subject.

12. A system according to claim 1, wherein the intervention determination module is configured to determine at least one intervention for reducing the contribution made by one of the plurality of factors, wherein the at least one intervention does not increase the contribution made by any other of the plurality of factors.

13. A computer-implemented method for assessing delirium in a subject with an apparatus, the apparatus comprising a memory comprising instruction data representing a set of instructions, and a processor configured to communicate with the memory and to execute the set of instructions, wherein the set of instructions, when executed by the processor, cause the processor to execute the method comprising:
receiving neural activity data for the subject;
determining whether the received neural activity is indicative that the subject is suffering from delirium;
receiving data relating to at least one factor of a plurality of factors which contribute to a cause of delirium, wherein the plurality of factors comprises a likelihood that the subject will develop an infection, wherein the likelihood that the subject will develop the infection is determined based on a measure of haematocrit levels of the subject; and
determining, based on the received data relating to the at least one factor, at least one intervention for reducing the contribution made by the at least one factor.

14. A computer-implemented method according to claim 13, further comprising:
indicating the determined at least one intervention to a medical professional.

15. An apparatus for assessing delirium in a subject, the apparatus comprising:
a memory comprising instruction data representing a set of instructions; and
a processor configured to communicate with the memory and to execute the set of instructions, wherein the set of instructions, when executed by the processor, cause the processor to:
receive neural activity data for the subject;
determine whether the received neural activity is indicative that the subject is suffering from delirium;
receive data relating to at least one factor of a plurality of factors which contribute to a cause of delirium, wherein the plurality of factors comprises a likelihood that the subject will develop an infection, wherein the likelihood that the subject will develop the infection is determined based on a measure of haematocrit levels of a subject; and
determine, based on the received data relating to the at least one factor, at least one intervention for reducing the contribution made by the at least one factor.

* * * * *